Feb. 1, 1955 H. M. TIRET Plant Pat. 1,345
FUCHSIA PLANT
Filed Feb. 27, 1952
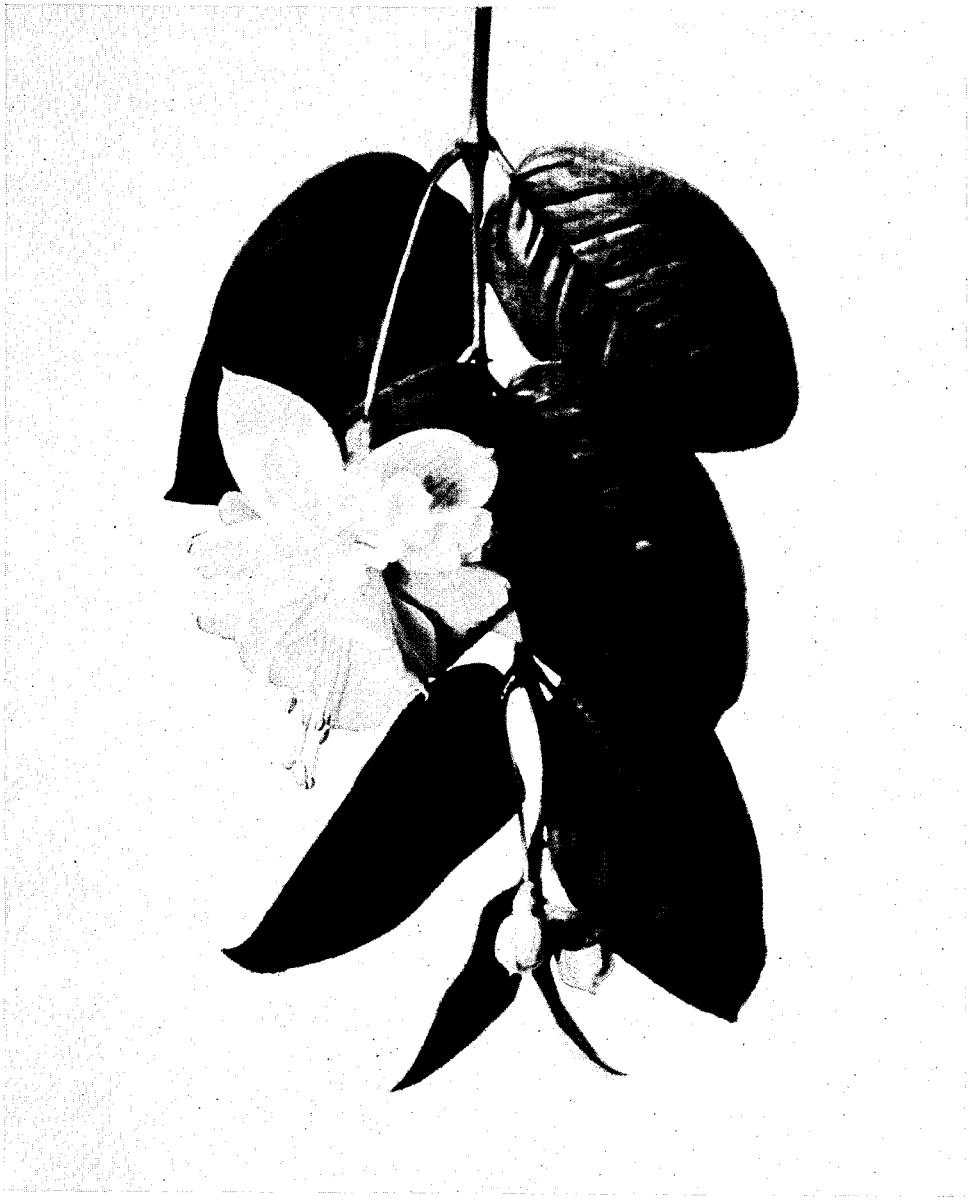
Inventor
Horace M. Tiret United States Patent Office Plant Pat. 1,345
Patented Feb. 1, 1955

1,345

FUCHSIA PLANT

Horace M. Tiret, San Francisco, Calif.

Application February 27, 1952, Serial No. 273,703

1 Claim. (Cl. 47—60)

The plant was derived as a hybrid from seedlings (unpatented) not introduced to the trade, namely 3/11/16 by 3/36/5, the figures representing applicant's own breeding symbols. The fuchsia plant is distinguished principally by its medium green foliage, medium vigorous habit of growth, exceptional size and form and all white coloring, which has not previously been found in this combination in any fuchsia plant. The plant has been asexually reproduced in Palo Alto, Santa Clara County, California, by cuttings which retained the characteristics of the parent fuchsia.

The plant is an upright variety, and grows with fair vigor. When the plant blooms, the large, globular white buds open into exceptionally large, very double flowers. The bud is white, as is the flower. Under certain growing conditions there may be a slight variation from the all white color in that the inside of the sepals and the outer surface of the smaller surrounding petals may be faintly blushed (pink). The flower has no fragrance.

A detailed description of this new variety of fuchsia plant follows:

*Habit of growth.*—Upright, willowy grower, fairly vigorous, which throws out branches from the roots and whose branches in turn are self branching. Flowers usually occur at the tips of the branches.

*Foliage.*—Large sized green leaves heavily creased, having serrated edges and evenly spaced along the branch. The leaves are broad and egg shaped. Buds are globular in shape and are white in color.

*Flower.*—The flower is very double and exceptionally large for the genus. The corolla is flaring with many smaller outer horizontal petals, giving it a very full effect. The fully opened flower is approximately 2⅝ inches in diameter. The flower is strongly resistant to wilting at high atmospheric temperature but grows equally well in the cooler coastal climate of the west. The form and the exceptionally large size of this white fuchsia are the outstanding, distinctive and different features of this plant. Under certain growing conditions there may be a slight variation from the all white color in that the underside of the sepals and the outer surface of the smaller surrounding petals may be faintly blushed (pink).

*Ovary.*—Short and stocky, light green in color.

*Tube.*—Medium long, medium thick, white in color.

*Petals.*—From fourteen to twenty petals occur to each flower, and the outer petals form a flaring skirt for the center petals. As the flower matures, the flaring effect is retained. The petals are white, except that under certain growing conditions there might be a slight blushed (pink) coloring of the outer surface of the outer surrounding petals as described.

*Stamens.*—The stamens are long, approximately 1⅝ inches in length, measured from the seed pod, and of a pink color, and terminate short of a long pistil, approximately 2¾ inches in length, measured from the seed pod, having a yellow tip which hangs below the cluster of stamens.

*Sepals.*—The sepals are very broad and medium long, colored white, with an average length of approximately 1¾ inches, and an average breadth of approximately 1 inch at the broadest point. Under certain growing conditions there may be a slight blushed (pink) coloring of the underside of the sepals. The texture is crepelike on the underside and smooth on the top.

*Parentage.*—Applicant's own seedlings (unpatented) and not introduced to the trade, applicant's own breeding symbols 3/11/16 by 3/36/5.

It is noted that the foliage and flowers will vary somewhat with the seasons and growing conditions: however, the fuchsia plant is clearly differentiated from others by the exceptionally large size and form of the flowers combined with their white coloring.

Having thus disclosed my discovery I claim:

A new and distinct variety of fuchsia plant, substantially as described and illustrated, characterized by flowers of exceptionally large size and form having white petals and very broad, medium long white sepals.

No references cited.